United States Patent [19]
Miltz

[11] Patent Number: 5,220,113
[45] Date of Patent: Jun. 15, 1993

[54] LETTUCE CULTIVAR BUD 71-3
[75] Inventor: David S. Miltz, Salinas, Calif.
[73] Assignee: Bud Antle, Inc., Salinas, Calif.
[21] Appl. No.: 381,491
[22] Filed: Jul. 18, 1989
[51] Int. Cl.⁵ ............................ A01H 5/00; A01H 5/10
[52] U.S. Cl. .................................... 800/200; 800/230; 800/255; 800/DIG. 13
[58] Field of Search ................... 800/1, 200, 230, 255, 800/DIG. 13; 47/58, DIG. 1

[56] References Cited
PUBLICATIONS

Guzman (1984) Circulars–Agr. Exp. Stat. Inst. of Food & Agr. Sci. U. of Florida (310) pp. 1–8.
Guzman (1982) Proc. Florida State Hort. Soc. (94) pp. 182–185.
Ryder (1986) in Breeding Vegetable Crops, Ed. by Bassett, Avi Publishing Co., Westport Conn., pp. 458–462.

*Primary Examiner*—Gary Benzion
*Attorney, Agent, or Firm*—Raymond Cranfill

[57] ABSTRACT

A lettuce cultivar of the Vanguard-group is disclosed which has heads having a mean diameter of 14 cm with medium green, glossy leaves, which is highly resistant to corky root rot and which is adapted to summer planting in mineral soils in summer cool regions along the Pacific Coast of North America.

4 Claims, 1 Drawing Sheet

LETTUCE CULTIVAR BUD 71-3

FIELD OF THE INVENTION

The present invention relates to cultivars of lettuce generally, and more particularly to cultivars of Vanguard-type lettuce.

BACKGROUND OF THE INVENTION

Lettuce, *Lactuca sativa* L., is a commercially important fresh leaf crop belonging to the aster family (Asteraceae) which includes such other important crops as sunflowers and artichokes. Lettuce is widely grown throughout the temperate and subtropical regions of the world, and is used predominantly as a fresh green in the human diet.

Lettuce originated from the ancestral wild species *L. sativa*. Today there are over one hundred cultivars which are divided in commerce into four large groups based on gross morphological characteristics of the gross leaf morphology and leaf arrangement: the Romaine (or Cos) Group, the Iceberg (or Crisp Head) Group, the Butterhead Group and the Loose Leaf Group. These basic lettuce types frequently form the basis for grouping lettuces as is commonly seen in supermarkets, grocery and produce stores. Each of these basic groups is comprised of numerous cultivars, each characterized by its own particular morphology, disease resistance, and cultural adaptations.

The present invention is directed to a novel cultivar within the Iceberg or Crisp Head lettuce group, by far the most popular group of lettuces sold. Iceberg Group lettuces are characterized basically by their relatively large, firm well formed heads. The leaves are spirally arranged on a stem with greatly foreshortened internodes, are tightly clasping upon one another and have a large water content, hence the name "Crisp Head". Within the Iceberg Groups there are several clusters or assemblages of related cultivars. One of these clusters is the Vanguard-type, named after the Vanguard cultivar which has served as one parent of the other Vanguard-type cultivars. Vanguard-type lettuce cultivars share the common characteristics of being adapted to the soils and climates of the desert growing region of western North America and possess in common certain morphological characteristics including:

1. Dark, dull-green outer leaves;
2. Coloration of leaves extending well down the leaf base towards the core;
3. Margins of the leaves being scalloped or undulate;
4. A softer leaf texture as compared to cultivars in the Great Lakes group;
5. Heads with creamy colored interiors.

Problems with existing cultivars adapted to western conditions include a general lack of significant resistance to corky root rot. This disease is caused by a pathogenic soil bacterium of the genus Rhizomonas and accounts for significant lettuce crop loss in the western United States, particularly in the Salinas and Santa Maria valleys. The bacterium attacks and destroys much of the root system, greatly reducing the ability of the lettuce plant to take up water and nutrients. Loss of the root system results in uneven stunted plants that are chlorotic and too small to harvest.

Unlike other leaf crops which are cooked and thus may be canned or otherwise processed, lettuce is almost universally sold as a fresh vegetable. Thus, its market ready appearance and perishability are key factors governing salability. Existing cultivars are often inferior because they produce heads which are undesirably small or which have loose or otherwise misshapen leaves. Leaf color of both external and internal head leaves is important for the reason that consumers desire richly colored greens for their salads and will pass over lettuce heads which are pale, clear or milky colored.

Existing Vanguard-type cultivars fail to exhibit all of the desired characteristics necessary for optimal production during the summer growing season. Vanguard is noted for its excellent coloring, particularly on leaves inside the head, its flat ribs and high quality, but is susceptible to a host of diseases including corky root rot, downy mildew, and tipburn, and is adapted for early spring harvest in the climate and soils of California's Imperial Valley and adjacent desert regions. Sea Green is most notable for its rich green color and its moderate resistance to big vein, but it is susceptible to corky root rot and tipburn, and is harvestable only in the spring. Salinas has been a popular cultivar adapted to the soils and climate of coastal California and is characterized by a resistance to bolting and tip burn, and by a dull green outer leaves with cream-colored interior leaves, and a relatively small head size of less than 13.5 cm. Salinas is not resistant to corky root rot. Montello is somewhat resistant to corky root rot, but is adapted to muck soils in the midwest and northeastern United States. It cannot be grown commercially in the coastal valleys of California.

Although Salinas and cultivars derived from it are adapted to the climates and soils of coastal California, there exists a need for an improved coastal cultivar of Iceberg-Group lettuce that has heads which are large in size and have a rich green color; which have more uniformly shaped, tightly clasping leaves which are adapted to summer growth and harvest; and which are resistant to corky root rot.

SUMMARY OF THE INVENTION

It is an object of the present invention to provide a lettuce cultivar that is adapted to the cool summer climate and soils prevalent along the west coast of the United States, particularly the coastal valleys of California.

It is another object of the present invention to provide a lettuce cultivar that is resistant to corky root rot.

It is yet another object of the present invention to provide a cultivar of lettuce that is comparable to Salinas in resistance to bolting during warm weather and long days.

It is a further object of the present invention to provide a lettuce cultivar which is large headed and firm, and has rich green leaves which are broad, regularly shaped and firmly overlapping.

The present invention meets these objectives by providing a novel Vanguard-type lettuce cultivar which is adapted for harvest in the cool summer climate along the United States west coast, which is resistant to corky root rot, and which is characterized by having large, firm heads with well formed, rich green, tightly overlapping leaves.

DETAILED DESCRIPTION OF THE INVENTION

Definitions

Figure 1:
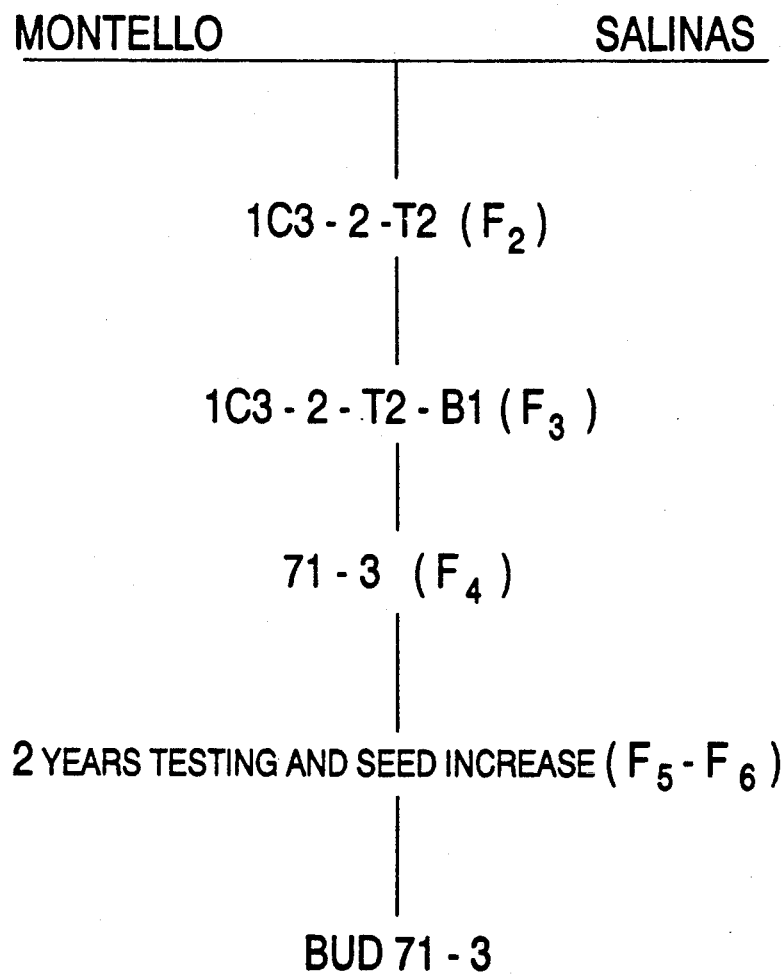
FIG. 1 is a genealogy of the lettuce cultivar of the present invention.

The following definitions will be helpful in the discussion of the BUD 71-3 cultivar that follows.

Cotyledon. In the case of lettuce, one of a pair of leaves formed on an embryo within a seed which upon germination are the first leaves to emerge.

Fourth Leaf. The fourth leaf formed on the lettuce plantlet subsequent to the emergence of the cotyledons.

Frame Leaf. The first set of freely recurring leaves which are external to the head.

Market Stage. The developmental stage reached by a crop plant at which time the plant is ready for harvest. In Iceberg Group cultivars of lettuce, it is that stage at which the head has reached a maximum size before bolting but in which most of the head leaves are still tightly clasping.

Market Trimmed. The harvested and trimmed head of lettuce which is ready to be packed and shipped to market.

Butt. The bottom portion of the lettuce head which includes the stem and adjacent leaf bases of the outermost head leaves.

Core. The stem of the lettuce head on which the leaves are borne.

Bolt. The process during which the stem within the lettuce head greatly elongates, causing the head to lose its shape and resulting ultimately in the producing of a flowering stalk.

Corky Root Rot. A disease of some lettuce cultivars caused by a pathogenic soil bacterium classified as a member of the genus Rhizomonas.

Origin and Parentage of BUD 71-3

Referring now to FIG. 1 the genealogy of lettuce cultivar of the present invention, herein designated as BUD 71-3, will now be described. BUD 71-3 is a Vanguard-type lettuce derived by pedigree selection after intercrossing cultivars Montello and Salinas. Pollen from Montello plants was used to fertilize female Salinas plants according to the mist depollination technique outlined by Ryder and Johnson, Hortscience 9: 584 (1974), which is incorporated by reference as though fully set forth herein. Montello is a lettuce cultivar well adapted to summer season in north central and northeastern Wisconsin muckland soils. Montello produces heads having a mean diameter similar to BUD 71-3 in the northeast, but produces substantially smaller heads when grown along the west coast of the United States. The leaves are moderately ribby and are finely dentate along the margin. The heads are unprotected and subject to sunscald. Montello is highly resistant to corky root rot, scoring a 1.3 on a scale of 0 to 5 wherein 0 represents complete resistance. Montello is not well adapted to the mineral soils of California, where it produces heads of below normal size which sunscald easily and which suffer early senescence.

Salinas is a lettuce cultivar well adapted to the mineral soils and cool summer of coastal western North America. Salinas produces heads having a mean diameter similar to BUD 71-3, except when infected with corky root rot when the head size is greatly diminished. The leaves are dull green in color, matching most closely 146A on the Royal Horticultural Society Color Chart, and have coarsely dentate to scalloped or wavy margins. The heads are adequately covered at maturity and are resistant to sunscald and tip burn. Salinas is susceptible to corky root rot, scoring a 5 on a scale of 0 to 5 where 0 represents complete resistance. Salinas is widely planted in summer-cool coastal valleys along the United States west coast.

In September 1982, 12 seeds from each of the lettuce cultivars Montello and Salinas were planted in greenhouse in Salinas, Calif. At flowering stage, the cultivars were intercrossed as described above. $F_1$ seed was harvested from eight successfully cross-fertilized Salinas plants and was massed in June 1983.

$F_1$ seed was planted in November 1983 and allowed to self pollinate. $F_2$ seed was harvested in June 1984. The $F_2$ seed was planted immediately thereafter and produced young lettuce plants by September 1983. From these plants, an individual was selected for resistance to corky root rot and for Vanguard-type leaves with smooth butt and desireable rich green color. This individual was designated IC3-2-T2, and allowed to go to seed.

In January 1985, $F_3$ seed was harvested from individual IC3-2-T2. This $F_3$ was planted shortly thereafter in Salinas. An individual designated IC3-2-T2-B1 was selected based upon the above described characteristics and was transplanted and allowed to go to seed.

In January 1986, $F_4$ seed produced by individual IC 3-2-T2-B1 was planted. Ten plants were selected out and designated and allowed to go to seed in July 1986. Seed from each of these plants was designated as a separate line, 71-1 through 71-10. Seed from each of these lines was immediately planted out in August 1986.

Line 71-3 was chosen for further development and seed increase. $F_5$ seed was produced by single seed descent and harvested in early 1987. The $F_5$ seed was planted in January of 1987 in Salinas in small trial plots. $F_6$ seed was produced by family selection increasing the seed from line 71-3 and was harvested in the Fall of 1987.

The $F_6$ seed was established in late 1987 at Salinas. The line was planted out in large trial plots and observed in the Summer of 1988. Thereafter the seed was harvested and bulked to produce the cultivar of the present invention, BUD 71-3.

Morphological Description of BUD 71-3

The lettuce cultivar BUD 71-3 will now be described. The terminology used herein to describe BUD 71-3 are those used by the Plant Variety Protection Office, unless otherwise noted, in PVPO Form LS-470-1, "Objective Description of Variety: LETTUCE."

1. PLANT TYPE. BUD 71-3 is a Vanguard-type lettuce cultivar. These are lettuce cultivars falling within the Iceberg or Crisp Head group of lettuces and are adapted to western climates and soils.

2. SEED. Seed is brown in color. Light is not required for germination, as is the case with some other lettuce cultivars. The seeds are susceptible to thermodormancy.

3. COTYLEDON TO FOURTH LEAF STAGE. Cotyledons upon emergence are spatulate. The fourth leaf is ovate with a length/width index (L/W × 10) of 15, with a coarsely dentate apical margin and a moderately dentate basal margin. The fourth leaf is further characterized by being moderately undulate, unrolled, slightly cupped, unreflexed, and having a medium green color (a rich green color similar to the cultivar Sea Green) without anthocyanic expression.

4. MATURE LEAVES. Mature leaves are broadly ovate, large, thick, moderately glossy and blistered, medium green in color, most closely matching color 146B of the Royal Horticultural Society Color Chart, with no anthocyanic expression (both external and outmost internal head leaves), leaf trichomes absent; margin with moderately deep incisions, crenate and moderately undulate as in the cultivar Vanguard.

5. PLANT AT MARKET STAGE. Frame leaves have a spread of about 41 cm. The heads are firm, spherical, and large having a diameter of about 14 cm with a standard deviation of 1.8 cm as measured on a market ready head having a single cap leaf, and weighing 768 gm with a standard deviation of 194 gm.

6. BUTT (BOTTOM OF MARKET-TRIMMED HEAD). The butt is rounded with moderately raised midribs on adjacent leaf bases.

7. CORE (STEM OF MARKET-TRIMMED HEAD). The core has a diameter of approximately 32 mm and a height of approximately 6.2 mm, as measured from base of head to stem apex within the head.

8. BOLTING. BUD 71-3 is a medium bolter as compared to the cultivar Salinas, taking approximately 141 days to bolt as measured from the time the seed first receives water sufficient for germination. The mature seed stalk reaches 127 cm in length, with total spread of the bolted plant reaching 42 cm. The bolter leaves (cauline leaves) are straight with dentate margins and are dark green in color. The inflorescence is largely terminal with some lateral shoots. Flowering basal side shoots are absent.

9. MATURITY. Plants of BUD 71-3 were planted in the northwest Salinas Valley, Calif. on Jun. 21, 1988 and matured to market-ready stage in approximately 70 days.

10. ADAPTATION. BUD 71-3 is adapted for summer planting along the United States west coast in mineral soils.

DISEASE AND STRESS REACTIONS: Bud 71-3 is highly resistant to corky root rot scoring a 1.8 on a 0 to 5 scale where 0 signifies complete resistance and 5 signifies complete susceptibility, and is somewhat resistant to tipburn and heat.

Propagation of BUD 71-3

Bud 71-3 may be propagated from seed or by tissue culture techniques.

Seed production is achieved by sowing existing seed in flats at 68°-70° F. Seedlings or young plantlets are then transferred to containers or beds and are grown at 85°-95° F. to induce bolting. The heads may need to be cut open or broken to permit elongation of the stem and inflorescence. Plants are allowed to self and the resulting seed are then collected.

Propogation may be had using explant material to produce leaf callus which is subsequently induced to form plantlets according to the methods described in Alconero, R. Hortscience 18:305-307 (1983), the contents of which are expressly incorporated herein.

Axial buds can be excised from existing plants and then can be induced to form rooted plants using techniques well known in the art.

Production Methods of BUD 71-3

Production of market ready lettuce from BUD 71-3 proceeds as follows. Seed is directly sown on double row beds of 40 in. centers. Rows on a bed are about 15 in. apart with seed deposited at intervals of 2 to 3 in. along the row.

Each seed is usually encapsulated in, or "pelleted," with inert clays to form a large and uniform pill. Encapsulation in this way facilitates positioning and planting of the seed which is small.

In California, the plants are watered during the germination phase using sprinkler systems. As the plants mature, watering is accomplished by irrigating the furrows between the rows.

Four to six weeks after germination, lettuce is thinned to produce a final stand in which plantlets are spaced apart in the row at distances of about 10 in.

In mineral soils common in the west, fertilization with nitrogen, phosphorus and, less frequently, potassium is required.

Harvest time varies according to the local climatic conditions. BUD 71-3 takes approximately 70 days from planting to harvest in the coastal valleys of California.

Deposit of BUD 71-3

Seeds of BUD 71-3 have been deposited with the American Type Culture Collection, 12301 Parklawn Dr., Rockville, Md. 20852. The deposit was made on Jun. 14, 1989 and received accession number ATCC 40618

Although the cultivar of the forgoing invention has been described and illustrated, it should be understood that certain changes and modifications may be practiced within the scope of this invention without departing from the scope of the invention as set forth in the accompanying claims.

I claim:

1. A lettuce cultivar designated BUD 71-3 as deposited with American Type Culture Collection under accession number 40618.
2. Propagation material of the plant of claim 1.
3. Pollen of the plant of claim 1.
4. Seeds of the plant of claim 1.

* * * * *